United States Patent [19]
Aung et al.

[11] Patent Number: 5,682,898
[45] Date of Patent: Nov. 4, 1997

[54] RESPIRATION RATE MEASURING APPARATUS

[75] Inventors: Ye Aung, Komaki; Yuji Matsubara, Nagoya, both of Japan

[73] Assignee: Colin Corporation, Aichi-ken, Japan

[21] Appl. No.: 423,448

[22] Filed: Apr. 19, 1995

[51] Int. Cl.$^6$ .................................................. A61B 5/00
[52] U.S. Cl. ......................... 128/671; 128/687; 128/721; 128/677; 128/671
[58] Field of Search ............................ 128/668, 670–2, 128/687–9, 716, 721

[56] References Cited

U.S. PATENT DOCUMENTS

| | | | |
|---|---|---|---|
| 5,022,402 | 6/1991 | Schieberl et al. | 128/689 |
| 5,119,822 | 6/1992 | Niwa. | |
| 5,143,078 | 9/1992 | Mather et al. | 128/671 |
| 5,179,956 | 1/1993 | Harada et al. | |
| 5,385,144 | 1/1995 | Yamanishi et al. | 128/671 |
| 5,396,893 | 3/1995 | Oberg et al. | 128/671 |

FOREIGN PATENT DOCUMENTS

A64-12505  1/1989  Japan.

*Primary Examiner*—Robert Nasser
*Attorney, Agent, or Firm*—Oliff & Berridge

[57] ABSTRACT

An apparatus is provided for measuring a respiration rate of a living subject, including a pulse rate measuring device which iteratively determines a pulse rate of the subject based on a pulse wave continuously produced from a peripheral portion of the subject; a systolic blood pressure measuring device which iteratively determines a systolic blood pressure of the subject based on a magnitude of a pressure pulse wave continuously produced from an arterial vessel of an extremity of the subject; a calculating device for iteratively calculating a product of two or more factors which include one of the iteratively determined pulse rates and one of the iteratively determined systolic blood pressures; and a respiration rate determining device for determining a respiration rate of the subject based on a period of a cyclic change of the iteratively calculated products. An apparatus is also provided for measuring a respiration rate of a living subject, including a pulse wave detecting device which detects a pulse wave continuously produced from the subject; a waveform evaluating device for iteratively providing an evaluated value of a waveform of the detected pulse wave; and a respiration rate determining device for determining a respiration rate of the subject based on a period of a cyclic change of the evaluated values iteratively provided by the waveform evaluating device.

11 Claims, 12 Drawing Sheets

RESPIRATION RATE MEASURING APPARATUS

BACKGROUND OF THE INVENTION

1. Field of the Invention

The present invention relates to an apparatus for measuring a respiration rate of a living subject based on information obtained from the circulatory organ of the living subject.

2. Related Art Statement

There have been proposed various sorts of respiration rate measuring devices, such as (a) a first device which determines a respiration rate of a living subject based on a period of cyclic change of temperatures of the expired and inspired gases of the living subject; (b) a second device which determines a respiration rate of a living subject based on a period of cyclic change of motions of the thorax of the living subject which motions are detected using a rubber tube wound around the thorax; and (c) a third device which determines a respiration rate of a living subject based on a period of cyclic change of impedances of the thorax of the living subject.

However, the above-indicated first to third conventional respiration rate measuring devices have the following problems: The first device requires that a temperature sensor such as a thermistor be secured with the help of a clip to the nose of the living subject so that the temperature sensor is located in a naris of the subject's nose and detects the temperatures of expired and inspired gases of the subject. Thus, the living subject, such as a patient, feels the pain or discomfort due to the use of the clip on his or her nose. The second device suffers from problems that the handling of the rubber tube is very cumbersome and that the second device may not be used on a patient having a disorder in his or her chest or abdomen. The third device requires that electrodes be attached to an exposed chest of a patient to detect impedances which change in relation with the respiration of the patient. Thus, the patient feels the discomfort due to the attachment of the electrodes to his or her chest. In addition, since the patient is required to expose his or her chest, the third device is not easy to use on the patient.

SUMMARY OF THE INVENTION

It is therefore an object of the present invention to provide a respiration rate measuring apparatus which is more easy to use, is applicable to a wider range of living subjects, and is free from the problem of discomfort felt by the subjects.

The above object has been achieved by the present invention. According to a first aspect of the present invention, there is provided an apparatus for measuring a respiration rate of a living subject, comprising: (a) a pulse rate measuring device which iteratively determines a pulse rate of the subject based on a pulse wave continuously produced from a peripheral portion of the subject in synchronism with heartbeat of the subject; (b) a systolic blood pressure measuring device which iteratively determines a systolic blood pressure of the subject based on a magnitude of a pressure pulse wave continuously produced from an arterial vessel of an extremity of the subject in synchronism with the heartbeat of the subject; (c) calculating means for iteratively calculating a product of at least two factors which include one of the pulse rates iteratively determined by the pulse rate measuring device and one of the systolic blood pressures iteratively determined by the systolic blood pressure measuring device; and (d) respiration rate determining means for determining the respiration rate of the subject based on a period of a cyclic change of the products iteratively calculated by the calculating means.

In the respiration rate measuring apparatus constructed as described above, the calculating means iteratively calculates a product of two or more factors including one of the pulse rate values provided by the pulse rate measuring device and one of the systolic blood pressure values provided by the systolic blood pressure measuring device, and the respiration rate determining means determines a respiration rate of the living subject based on a period of cyclic change of the products iteratively provided by the calculating means. The pulse rate measuring device iteratively determines a pulse rate value of the subject based on a pulse wave which is continuously produced from a peripheral portion of the subject in synchronism with heartbeat of the subject, and the systolic blood pressure measuring device iteratively determines a systolic blood pressure value of the subject based on a magnitude of a pressure pulse wave which is continuously produced from an arterial vessel of an extremity of the subject in synchronism with the heartbeat of the subject. Thus, the present apparatus is much more easily used, and is applicable to much wider a range of living subjects, than the conventional respiration-rate measuring devices wherein a temperature sensor is secured using a clip to the nose of a subject, a rubber tube is wound around the chest of a subject, or electrodes are attached to an exposed chest of a subject. In addition, the present apparatus does not cause the living subject to feel discomfort due to the use thereof on the subject.

In a preferred embodiment in accordance with the first aspect of the invention, the calculating means comprises means for iteratively calculating, as the product of the at least two factors, a value, N–PRP(t), according to a following expression:

$$N\text{--}PRP(t)=PR(t)\times[SYS(t-i)/n]$$

where

PR(t) is a pulse rate determined by the pulse rate measuring device,

SYS(t) is a systolic blood pressure determined by the systolic blood pressure measuring device, t is time, i is a time lag between PR(t) and SYS(t–i), and n is a number greater than one.

In the above embodiment, the time lag i may be a constant value. Alternatively, the calculating means may further comprise means for iteratively determining the time lag i by calculating a time difference between (a) a time of occurrence of each of successive upper peaks of a first curve representing the pulse rates PR(t) iteratively determined by the pulse rate measuring device and (b) a time of occurrence of a corresponding one of successive upper peaks of a second curve representing the systolic blood pressure values SYS(t) iteratively determined by the systolic blood pressure measuring device.

According to a second aspect of the present invention, there is provided an apparatus for measuring a respiration rate of a living subject, comprising: (A) a pulse wave detecting device which detects a pulse wave continuously produced from the subject in synchronism with heartbeat of the subject; (B) waveform evaluating means for iteratively providing an evaluated value of a waveform of the pulse wave detected by the pulse wave detecting device; and (C) respiration rate determining means for determining the respiration rate of the subject based on a period of a cyclic change of the evaluated values iteratively provided by the waveform evaluating means.

In the respiration rate measuring apparatus constructed as described above, the waveform evaluating means iteratively provides an evaluated value of a waveform of the pulse wave detected by the pulse wave detecting device, and the respiration rate determining means determines a respiration rate of the living subject based on a period of cyclic change of the evaluated values iteratively provided by the waveform evaluating means. The pulse wave detecting device detects a pulse wave which is continuously produced from the subject in synchronism with heartbeat of the subject. Thus, the present apparatus is much more easy to use, and is applicable to much wider a range of living subjects, than the conventional respiration-rate measuring devices wherein a temperature sensor is secured with the help of a clip to the nose of a subject, a rubber tube is wound around the chest of a subject, or electrodes are attached to an exposed chest of a subject. Additionally, the present apparatus does not cause the living subject to feel discomfort due to the use thereof on the subject.

In a preferred embodiment in accordance with the second aspect of the invention, the pulse wave comprises a plurality of successive pulses each of which corresponds to a cycle of heartbeat of the subject, the waveform evaluating means comprising area calculating means for iteratively calculating, in a coordinate system defined by a first axis representing time and a second axis representing magnitudes of the pulse wave, an area of each of the successive pulses which is bounded by (a) a waveform of the each pulse obtained in a predetermined time duration following a time of occurrence of an upper peak of the each pulse and (b) a reference line parallel to the first axis, the area calculating means iteratively providing the calculated area as the evaluated value of the waveform of the pulse wave. The predetermined time duration may be equal to half a period, $T_M$, of cyclic change of the pulse wave, i.e., equal to a value, $T_M/2$. The value $T_M$ may be a prescribed constant value.

In another embodiment in accordance with the second aspect of the invention, the pulse wave comprises a plurality of successive pulses each of which corresponds to a cycle of heartbeat of the subject, the waveform evaluating means comprising descending-portion evaluating means for iteratively providing, as the evaluated value of the waveform of the pulse wave, an evaluated value of a waveform of a descending portion of the each pulse following a time of occurrence of an upper peak of the each pulse. In this embodiment, the descending-portion evaluating means may calculate, as the evaluated value of the waveform of the descending portion of the each pulse, an area of a triangle, ABC, defined by (a) a first point, A, located on the upper peak of the each pulse, (b) a second point, B, located on the descending portion at a first predetermined time after the first point A, and (c) a third point, C, located on the descending portion at a second predetermined time after the second point B. Each of the first and second predetermined times may be equal to one fourth of a period, $T_M$, of cyclic change of the pulse wave. The period $T_M$ may be a prescribed constant value.

In yet another embodiment in accordance with the second aspect of the invention, the pulse wave detecting device comprises a pressure pulse wave sensor which detects a pressure pulse wave continuously produced from an arterial vessel of an extremity of the subject in synchronism with the heartbeat of the subject. The arterial vessel of the subject's extremity may be a radial artery or a pedal dorsal artery.

Otherwise, the pulse wave detecting device may comprise a sensor or detector which detects a finger-tip pulse wave, a volumetric pulse wave, or a photoelectric pulse wave, from a finger or a toe of a living subject.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
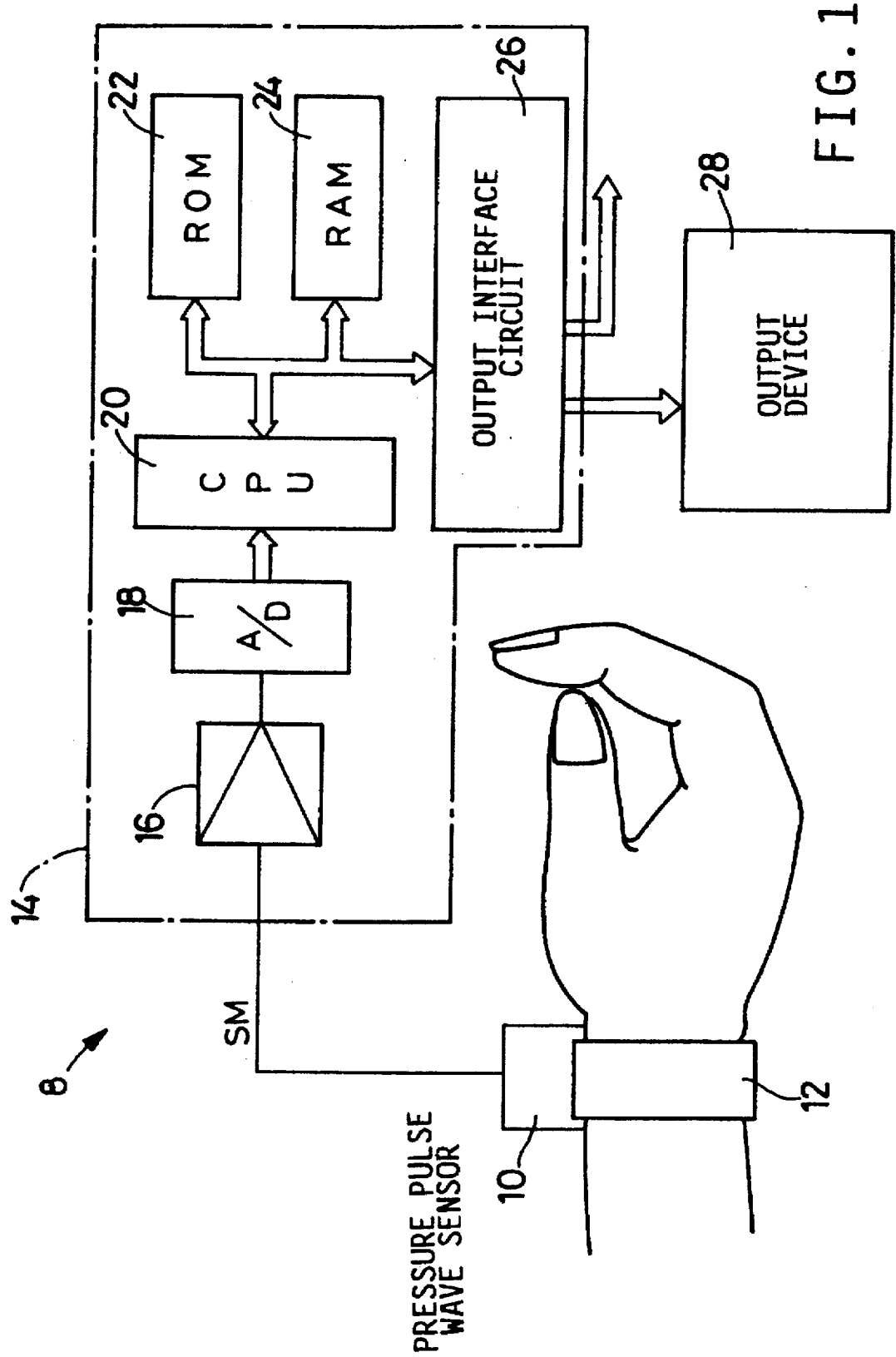
FIG. 1 is a diagrammatic view of a respiration rate measuring apparatus embodying the present invention.
Figure 2:
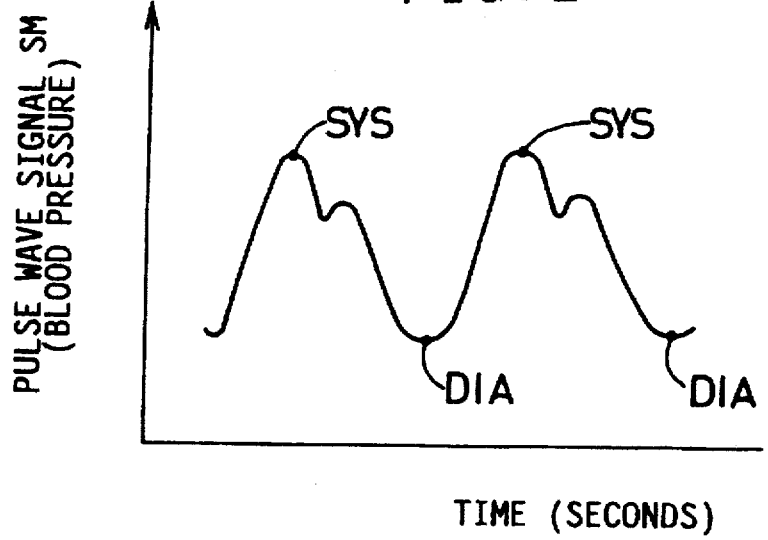
FIG. 2 is a graph showing a pulse wave signal, SM, produced by a pressure pulse wave sensor of the apparatus of FIG. 1.

Referring first to FIG. 1, there is shown a respiration-rate measuring apparatus 8 embodying the present invention. In the figure, reference numeral 10 designates a pressure pulse wave sensor disclosed in, for example, U.S. Pat. No. 5,179, 956. The pulse wave sensor 10 detects a pressure pulse wave which is produced from a radial artery of a wrist of a living subject such as a patient. The pulse wave sensor 10 includes (a) a press member (not shown) having a press surface in which a plurality of pressure sensing elements (e.g., diodes) are provided in an array; and a pressing device (not shown) for pressing the press member against the radial artery via the subject's skin such that the array of pressure sensing elements substantially perpendicularly intersects the radial artery. The pulse wave sensor 10 is worn on the wrist of the subject with the help of a band 12. As disclosed in U.S. Pat. No. 5,119,822 or Unexamined Japanese Patent Application laid open under Publication No. 64(1989)-12505, the pressing force applied to the press member from the pressing device is maintained at an optimum force, so that a portion of the wall of the radial artery is deformed to be flat under the press member. Pressure values measured by the pressure sensing elements of the pulse wave sensor 10 located directly above the flattened wall of the radial artery, accurately represent intra-arterial blood pressure values inside the radial artery. Therefore, an upper-peak and a lower-peak magnitude of the pressure pulse wave detected by the pulse wave sensor 10 accurately correspond to a systolic blood pressure, SYS, and a diastolic blood pressure, DIA, of the subject, respectively. FIG. 2 shows a waveform of a pressure pulse wave detected from a living subject by the pulse wave sensor 10. As shown in FIG. 2, the pressure pulse wave detected by the pulse wave sensor 10 includes successive pulses each of which is produced from the radial artery of the subject in synchronism with a cycle of heartbeat of the subject. Each pulse has an upper peak corresponding to a systolic blood pressure SYS and a lower peak corresponding to a diastolic blood pressure DIA of the subject.

The pulse wave sensor 10 generates a pulse wave signal, SM, representing the pressure pulse wave detected thereby from the radial artery of the living subject. FIG. 2 shows the change of the pulse wave signal SM with respect to time in terms of seconds. The pulse wave signal SM is supplied to a respiration-rate measure circuit 14 which determines a respiration rate of the subject based on the pulse wave signal SM. The measure circuit 14 includes an amplifier 16 for amplifying the pulse wave signal SM supplied thereto, and an analog to digital (A/D) converter 18 for converting the amplified, analog signal SM into a digital signal SM. The measure circuit 14 further includes a central processing unit (CPU) 20, a read only memory (ROM) 22, a random access memory (RAM) 24, and an output interface circuit 26 which cooperate with one another to provide a so-called microcomputer. The CPU 20 processes the input signal SM, and calculates a respiration rate of the living subject, according to a control program pre-stored in the ROM 22 and by utilizing a temporary-storage function of the RAM 24. The CPU 20 controls an output device 28 to display the thus determined respiration rate of the subject on a display (not shown) such as a cathode ray tube (CRT) or a liquid crystal display (LCD), and record the same on a recording medium (not shown) such as a magnetic disk or a recording sheet, and additionally transmits the thus collected respiration rate data to other devices, as needed.

The respiration-rate measure circuit 14, or CPU 20 thereof, iteratively determines a cycle or period, $T_M$, of pulse wave signal SM by calculating a time difference between respective upper (or lower) peaks of two successive pulses corresponding to two successive cycles of heartbeat of the living subject. The CPU 20 determines, based on the thus determined period $T_M$, a pulse rate, PR $(=60/T_M)$, of the subject in terms of a number of pulses per minute. Thus, upon detection of each pulse corresponding to one cycle of heartbeat of the subject, the CPU 20 determines a pulse rate PR of the subject. The pulse rate values, PR(t), iteratively determined by the CPU 20 change as a function of time.

In addition, the CPU 20 iteratively determines a systolic blood pressure SYS of the living subject corresponding to the upper-peak magnitude of each pulse of pulse wave signal SM, according to a known algorithm pre-stored in the ROM 22. The systolic blood pressure values, SYS(t), iteratively determined by the CPU 20 also change as a function of time.

Furthermore, the CPU 20 iteratively calculates a product or value, N-PRP(t), based on a pulse rate value PR(t) and a systolic blood pressure value SYS(t-i), according to a following expression (1):

$$N\text{-}PRP(t)=PR(t)\times[SYS(t-i)/n] \qquad (1)$$

where t is time, i is a time lag between PR(t) and

SYS(t-i), and n is a number greater than one.

Figure 3:
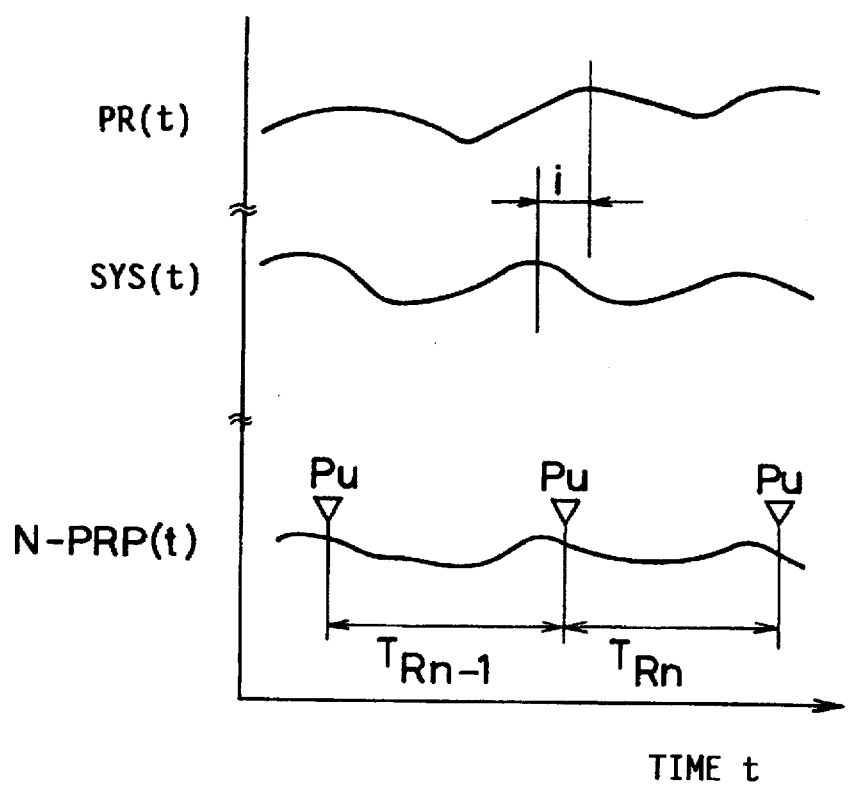
FIG. 3 is a time chart showing a curve representing the time change of pulse rate values, PR(t), a curve representing the time change of systolic blood pressure values, SYS(t), and a curve representing the time change of calculated values, N−PRP(t), each obtained by the apparatus of FIG. 1.

The number n is used to reduce the arithmetic weight of values SYS(t) relative to that of values PR(t). For example, two may be employed as the number n (i.e., n=2). The time lag i is a time difference between an upper peak of a curve representing the time change of values PR(t) and a corresponding upper peak of a curve representing the time-change of values SYS(t), as shown in FIG. 3. The value i may be a prescribed constant value determined, for example, from an average time lag of many people. Otherwise the value i may be determined by the measure circuit 14, based on the measured values PR(t), SYS(t), according to a control program pre-stored in the ROM 22.

Finally, the CPU 20 determines a period, TR, (unit: seconds) of cyclic change of the values N-PRP(t) and determines, based on the thus determined period $T_R$, a respiration rate, RR $(=60/T_R)$, of the living subject in terms of a number of respirations per minute. The manner of determination of the values N-PRP(t) will be described in detail later. FIG. 3 shows three curves respectively representing the respective time changes of pulse rate values PR(t), systolic blood pressure values SYS(t), and calculated values N-PRP(t). The CPU 20 repeats this process and iteratively measures the respiration rate values of the living subject.

Next, there will be described the operation of the respiration-rate measuring apparatus 8, or the measure circuit 14 thereof, by reference to the flow chart of FIG. 4.

First, at Step SS1, the CPU 20 judges whether the CPU 20 has received a pulse wave signal SM from the pressure pulse wave sensor 10, more specifically, whether the CPU 10 has identified an upper peak of one pulse corresponding to one cycle of heartbeat of the living subject. If a negative judgment is made at Step SS1, the CPU 20 waits for supplying of the one-pulse signal SM. Meanwhile, if a positive judgment is made at Step SS1, the control of the CPU 20 proceeds with Step SS2 to determine a period $T_M$ of the pulse wave signal SM, by calculating a time difference between respective upper (or lower) peaks of two successive pulses of the signal SM and determine, based on the thus determined period $T_M$, a pulse rate PR $(=60/T_M)$ of the subject as the number of pulses per minute. Thus, the CPU 20 iteratively determines a pulse rate value PR upon supplying of each one-pulse signal SM. FIG. 3 shows a curve representing the iteratively determined pulse rate values PR(t) as a function of time.

Step SS2 is followed by Step SS3 to determine a systolic blood pressure SYS of the living subject corresponding to the upper-peak magnitude of the one-pulse signal SM obtained at Step SS1, according to a known algorithm pre-stored in the ROM 22. The CPU 20 iteratively determines a systolic blood pressure value SYS upon supplying of each one-pulse signal SM. FIG. 3 shows a curve representing the iteratively determined systolic blood pressure values SYS(t) as a function of time.

At the following Step SS4, the CPU 20 calculates, according to the above-explained expression (1), a product N–PRP (t) based on the value PR(t) determined at Step SS2 and the value SYS(t–i) determined at Step SS3 prior to the value PR(t) by the time lag i. The CPU 20 iteratively determines a product N–PRP upon supplying of each one-pulse signal SM. FIG. 3 shows a curve representing the iteratively determined products N–PRP(t) as a function of time. Step SS4 corresponds to calculating means for iteratively calculating a product of two or more factors including a pulse rate, and a systolic blood pressure, of a living subject.

Step SS4 is followed by Step SS5 to judge whether at least one of the two curves or waves PR(t), SYS(t) has a fluctuation, i.e., wave amplitude smaller than a reference value. If a negative judgment is made, the control of the CPU 20 goes to Step SS6 to subject the curve or wave N–PRP(t) to a known median filter treatment, thereby smoothing the waveform of the wave N–PRP(t). The median filter treatment is carried out in such a way that an odd number (e.g., three or five) of successive data points of the wave N–PRP(t) are sequentially selected and compared with one another and the time-wise center data point is replaced by the magnitude-wise median data point. By removing the oldest data point and adding the next, new data point, this process is repeated with respect to all the data points of the wave N–PRP. Step SS6 is followed by Step SS7 to identify an upper peak of the wave N–PRP(t). On the other hand, if a positive judgment is made at Step SS5, the control of the CPU 20 skips Step SS6 and directly goes to Step SS7.

If a positive judgment is made at Step SS7, the control of the CPU 20 goes to Step SS8 to determine a current period, $T_{Rn}$, by calculating a time difference between a preceding upper peak, $P_u$, determined at Step SS7 in the preceding control cycle and a current upper peak, $P_u$, determined at Step SS7 in the current control cycle, and judging whether the thus determined current period $T_{Rn}$ is not greater than half the smaller one of the respective periods of the two waves PR(t), SYS(t). Step SS8 is provided for removing an erroneously determined, i.e., "abnormal", upper peak of the curve N–PRP(t). If a positive judgment is made at Step SS8, the control of the CPU 20 goes back to Step SS1 and the following steps. On the other hand, if a negative judgment is made, the control proceeds with Step SS9 to determine, based on the period of cyclic change of the wave N–PRP(t), i.e., respiration period $T_{Rn}$ of the living subject, a respiration rate RR of the subject in terms of a number of respirations per minute, according to the following expression (2), and subsequently control the output device 28 to output the thus determined respiration rate value RR:

$$RR=60/[(T_{Rn-3}+T_{Rn-2}+T_{Rn-1}+T_{Rn})/4]$$

where $T_{Rn-3}$ is a respiration period determined before three control cycles;

$T_{Rn-2}$ is a respiration period determined before two control cycles; and $T_{Rn-1}$ is the preceding respiration period determined before one control cycle, i.e., in the preceding control cycle.

Steps SS7, SS8 and SS9 correspond to respiration-rate determining means for determining a respiration rate of a living subject based on a period of cyclic change of the products iteratively calculated by the calculating means.

If a negative judgment is made at Step SS7, the control of the CPU 20 goes to Step SS10 to judge whether a time measured from the preceding upper peak of the curve N–PRP(t) identified in the preceding control cycle, has exceeded the preceding respiration period $T_{Rn-1}$ determined in the preceding control cycle and simultaneously each of the two curves PR(t), SYS(t) has had an upper peak thereof corresponding to an upper peak of the curve N–PRP(t) which should have been identified in the current control cycle. If a negative judgment is made at Step 10, the CPU 20 estimates that there is no respiration of the living subject. Thus, the control of the CPU 20 returns to Step SS1 and the following steps. On the other hand, a positive judgment made at Step SS10 means that the curve N–PRP(t) has not had a distinctive and identifiable upper peak, and therefore the CPU 20 assumes that the curve N–PRP(t) has had an upper peak thereof at the same respiration period as that of the preceding respiration period $T_{Rn-1}$. That is, the CPU 20 assumes that the current respiration rate $T_{Rn}$ is equal to the preceding respiration rate $T_{Rn-1}$. Then, the control of the CPU 20 goes to Step SS9.

Figure 4:
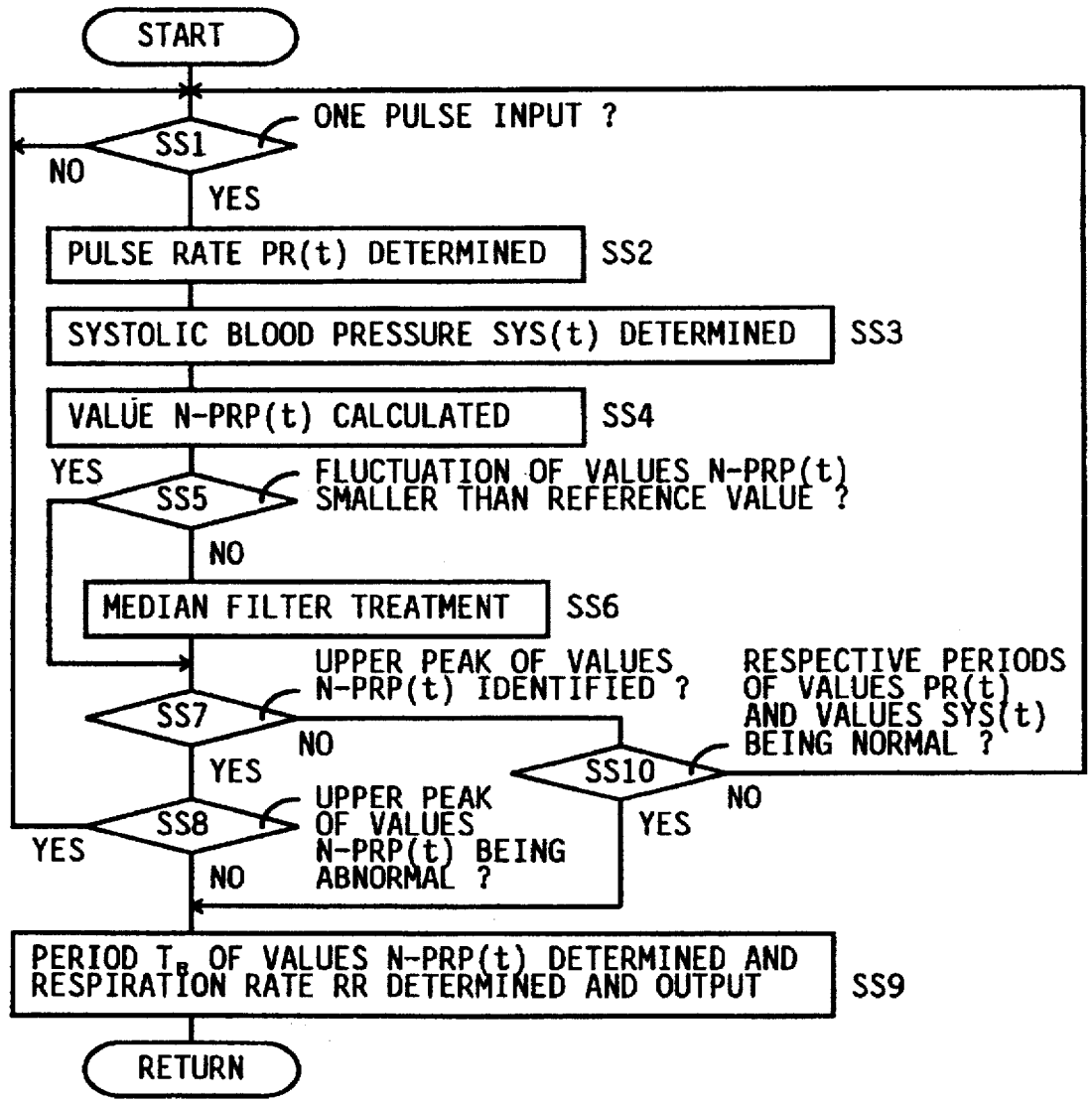
FIG. 4 is a flow chart representing a control program according to which the apparatus of FIG. 1 is operated.

While the control routine of FIG. 4 is repeated, the CPU 20 iteratively calculates a product N–PRP based on an iteratively determined pulse rate PR and an iteratively determined systolic blood pressure SYS, according to the expression (1), and iteratively calculates a respiration rate RR based on the period of cyclic change of products N–PRP. With the present respiration-rate measuring apparatus 8, the measurement of respiration rate of a living subject is carried out by just wearing the pulse wave sensor 10 around a wrist of the living subject. Thus, the present apparatus 8 is much easier to use, and is applicable to much wider a range of living subjects, than the conventional respiration-rate measuring techniques wherein a temperature sensor is fixed using a clip to the nose of a subject, a rubber tube is wound around the chest of a subject, or electrodes are attached to the exposed chest of a subject. In addition, the present apparatus 8 does not cause a living subject to feel discomfort due to the use thereof on the subject.

Figure 5:
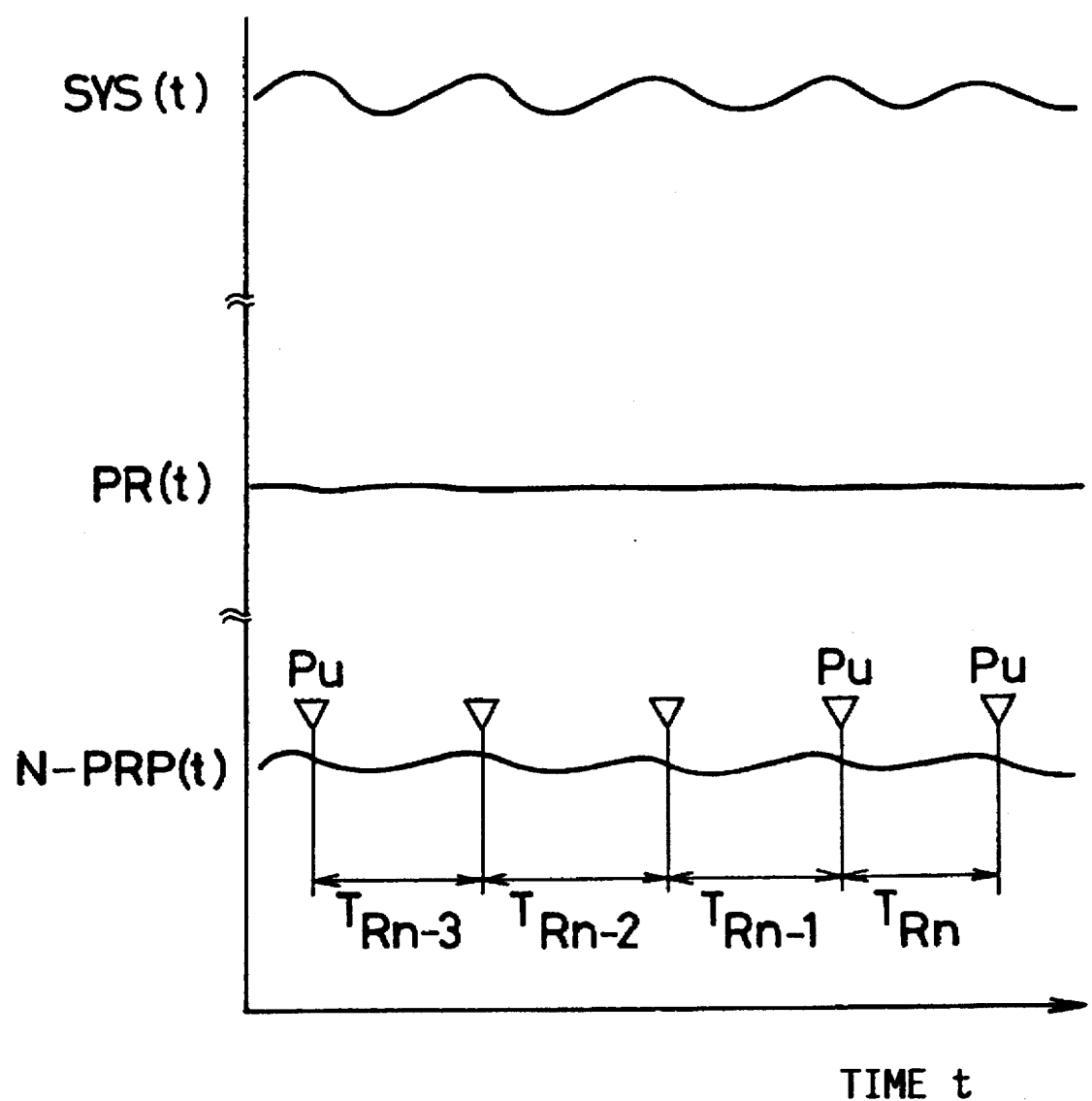
FIG. 5 is a time chart showing a time-change curve of pulse rate values PR(t), a time-change curve of systolic blood pressure values SYS(t), and a time-change curve of calculated values N−PRP(t), each obtained by the apparatus of FIG. 1 from a patient who is cared depending on an artificial respiratory machine.

In a particular case where a patient is cared depending on an artificial respiratory machine, the pulse rates PR(t) obtained from such a patient have substantially no change as shown in FIG. 5. However, the expression (1) advantageously functions to accurately measure respiration rates RR of the patient.

Next, there will be described a second embodiment of the present invention. The second embodiment also relates to a respiration rate (RR) measuring apparatus and has the same hardware construction as that of the first embodiment shown in FIG. 1. Thus, the same reference numerals as used in FIG. 1 are used to refer to the corresponding elements of the second embodiment, and the description of those elements is not repeated. However, the RR measuring apparatus as the second embodiment is operated according to a control program represented by the flow chart of FIG. 6 in place of the control program represented by the flow chart of FIG. 4. The present apparatus determines a respiration rate RR of a living subject, such as a patient, based on the change of waveform of a pulse wave signal SM supplied from a pressure pulse wave sensor 10.

In the second embodiment, the pulse wave sensor 10 detects a pressure pulse wave produced from an artery of the patient in synchronism with heartbeat of the patient, and supplies a pulse wave signal SM representing the detected pressure pulse wave, to a respiration-rate measure circuit 14. The measure circuit 14, or CPU 20 of the circuit 14, determines a period of cyclic change of the waveform of the pulse wave signal SM, and calculates a respiration rate RR of the patient based on the determined period of the waveform of pulse wave signal SM.

Figure 6:
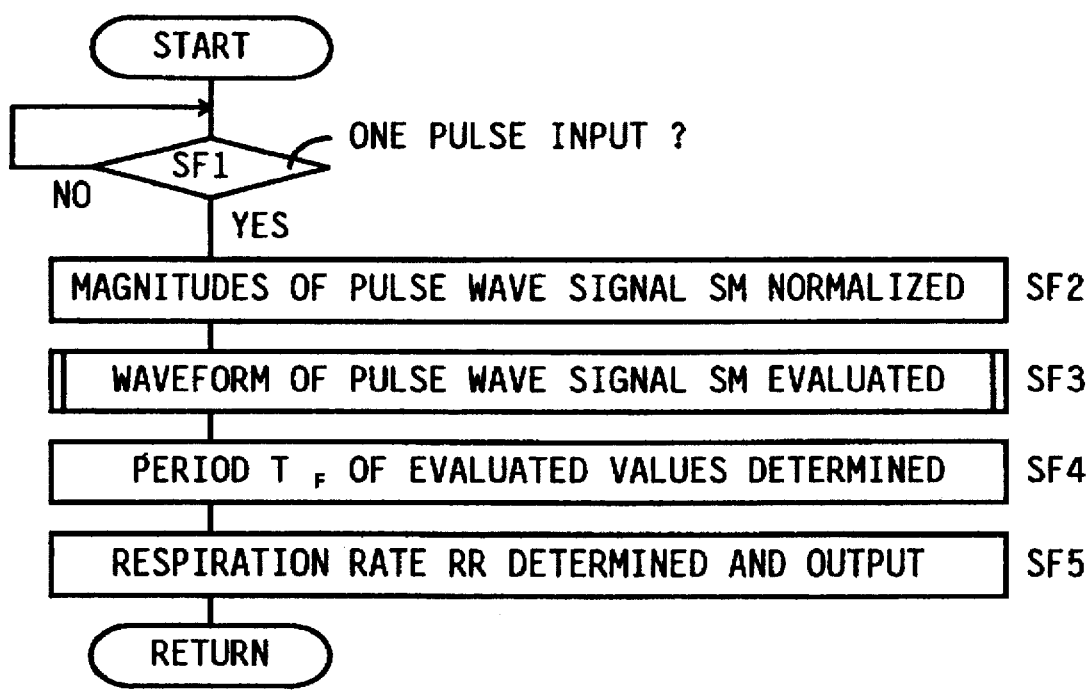
FIG. 6 is a flow chart representing a control program employed in another respiration rate measuring apparatus as a second embodiment of the invention.

Hereinafter, there will be described the operation of the respiration-rate measure circuit 14 in accordance with the second embodiment, by reference to the flow chart of FIG. 6.

Figure 7:
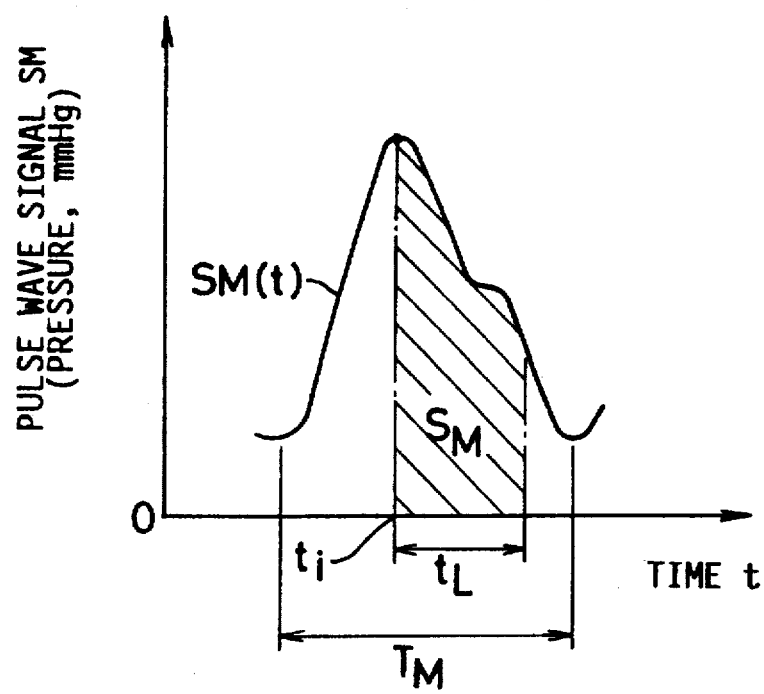
FIG. 7 is a graph showing an area, $S_M$, as an evaluated value of the waveform of a specific portion of a pulse wave signal SM obtained by a pulse wave sensor in the second embodiment.

First, at Step SF1, the CPU 20 judges whether the measure circuit 14 has received, from the pulse wave sensor 10, a length of pulse wave signal SM corresponding to a period of cyclic change (i.e., one pulse) of the signal SM, i.e., corresponding to a cycle of heartbeat of the patient. If a negative judgment is made at Step SF1, the CPU 20 waits for a positive judgment to be made at Step SF1. Once a positive judgment is made at this step, the control of the CPU 20 proceeds with Step SF2 to normalize the waveform of pulse wave signal SM by adjusting the respective magnitudes of signal SM so that those magnitudes (i.e., waveform) lie within a prescribed range, and subsequently to Step SF3 to quantify or evaluate the waveform of a portion of the normalized one-period signal SM. FIG. 7 shows a length of pulse wave signal SM(t) corresponding to one period, $T_M$, of cyclic change of the signal SM(t). At Step SF3, the CPU 20 calculates an area, $S_M$, bounded by (a) the waveform of a specific portion of one-period signal SM obtained in a predetermined time duration, $t_L$, (e.g., half the period $T_M$, i.e., $T_M/2$) following an upper peak, $t_i$, of the one-period signal SM and (b) a reference base line corresponding to the zero mmHg pressure, according to the following expression (3):

$$S_M = \sum_{t=t_i}^{t_i+T_M/2} SM(t) \quad (3)$$

The respective areas $S_M$ of successive one-period signals SM change with the time change of the respective waveforms of the specific portions of the successive one-period signals SM following the respective upper peaks thereof.

Step SF3 is followed by Step SF4 to determine a period, $T_F$, of cyclic change of the respective areas $S_M$ of the successive one-period signals SM, by calculating a time difference between two successive upper peaks of the areas $S_M$. At the following Step SF5, the CPU 20 determines a respiration rate RR of the patient from the thus determined period $T_F$, according to the following expression (4):

$$RR = 60/[(T_{Fn-3} + T_{Fn-2} + T_{Fn-1} + T_{Fn})/4] \quad (4)$$

where $T_{Fn-3}$ is a respiration period determined before three control cycles;

$T_{Fn-2}$ is a respiration period determined before two control cycles; and $T_{Fn-1}$ is the preceding respiration period determined before one control cycle, i.e., in the preceding control cycle.

At Step SF5, the CPU 20 controls an output device 28 to display the determined value RR on a cathode ray tube (CRT, not shown) and record the same on a recording sheet. The waveform of a specific portion of one-pulse signal SM following the upper peak thereof highly correlates with the respiration of a living subject, and the area $S_M$ obtained from the one-pulse signal SM represents the waveform of the specific portion of the one-pulse signal SM following the upper peak thereof. Thus, a periodic change of the respective areas $S_M$ obtained from successive one-pulse signals SM represent a respiration rate of the living subject. In the present embodiment, Step SF3 corresponds to waveform evaluating means, and Steps SF4 and SF5 correspond to respiration rate determining means.

With the respiration rate measuring apparatus in accordance with the second embodiment, too, the measurement of respiration rate of a living subject is carried out by just wearing the pulse wave sensor 10 around a wrist of the subject. Thus, the present apparatus is much more easy to use, and is applicable to much wider a range of living subjects, than the conventional respiration-rate measuring device wherein a temperature sensor is fixed using a clip to the nose of a subject, a rubber tube is wound around the chest of a subject, or electrodes are attached to an exposed chest of a subject. In addition, the present apparatus does not cause a living subject to feel any discomfort due to the use thereof on the subject.

Additionally, in the second embodiment, since the respective magnitudes of each one-pulse wave signal SM are normalized at Step SF3, the respective areas $S_M$ of successive one-pulse signals SM are free from adverse influences due to the fluctuation of respective systolic blood pressure values SYS of the successive one-pulse signals SM. Moreover, since each area $S_M$ is bounded by the reference base line corresponding to the 0 mmHg pressure, the respective areas $S_M$ of the successive one-pulse signals SM are free from adverse influences due to the fluctuation of respective diastolic blood pressure values DIA of the successive one-pulse signals SM. Furthermore, since each area $S_M$ is defined by the waveform of a specific portion of one-pulse signal SM obtained in a predetermined time duration $t_L$, the respective areas $S_M$ of the successive one-pulse signals SM are free from adverse influences due to the fluctuation of respective pulse rate values PR of the successive one-pulse signals SM.

There will be described a third embodiment of the present invention. While, in the second embodiment, at Step SF3 of FIG. 6 the area $S_M$ of each one-pulse signal SM is obtained according to the expression (3), for providing an evaluated value of the waveform of a specific portion of each one-pulse signal SM which closely relates to the respiration rate RR of the patient, the expression (3) is replaced in the third embodiment by the following expression (5), for obtaining a weighted area, $S_{MO}$:

$$S_{MO} = \sum_{t=t_i}^{t_i+T_M/2} SM(t) \times [(t_i + T_M/2) - t] \quad (5)$$

Figure 8:
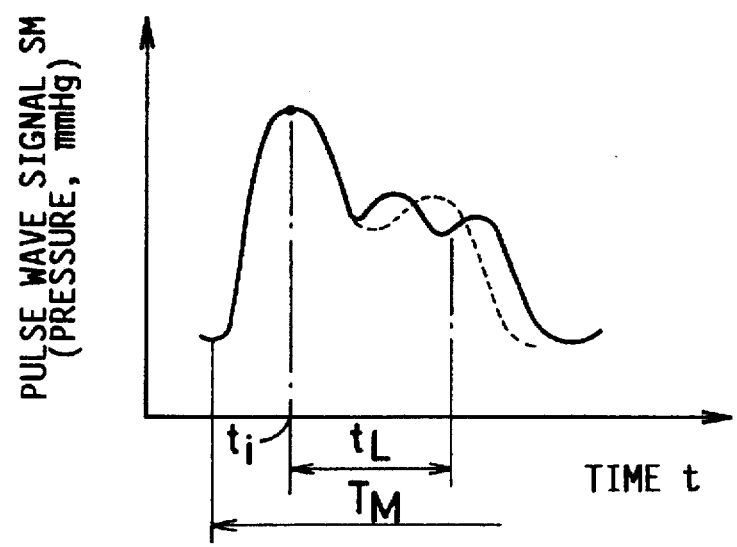
FIG. 8 is a graph showing two pulse wave signals SM having different waveforms which provide an identical area $S_M$ but are identified from each other in a third embodiment of the present invention.
Figure 9:
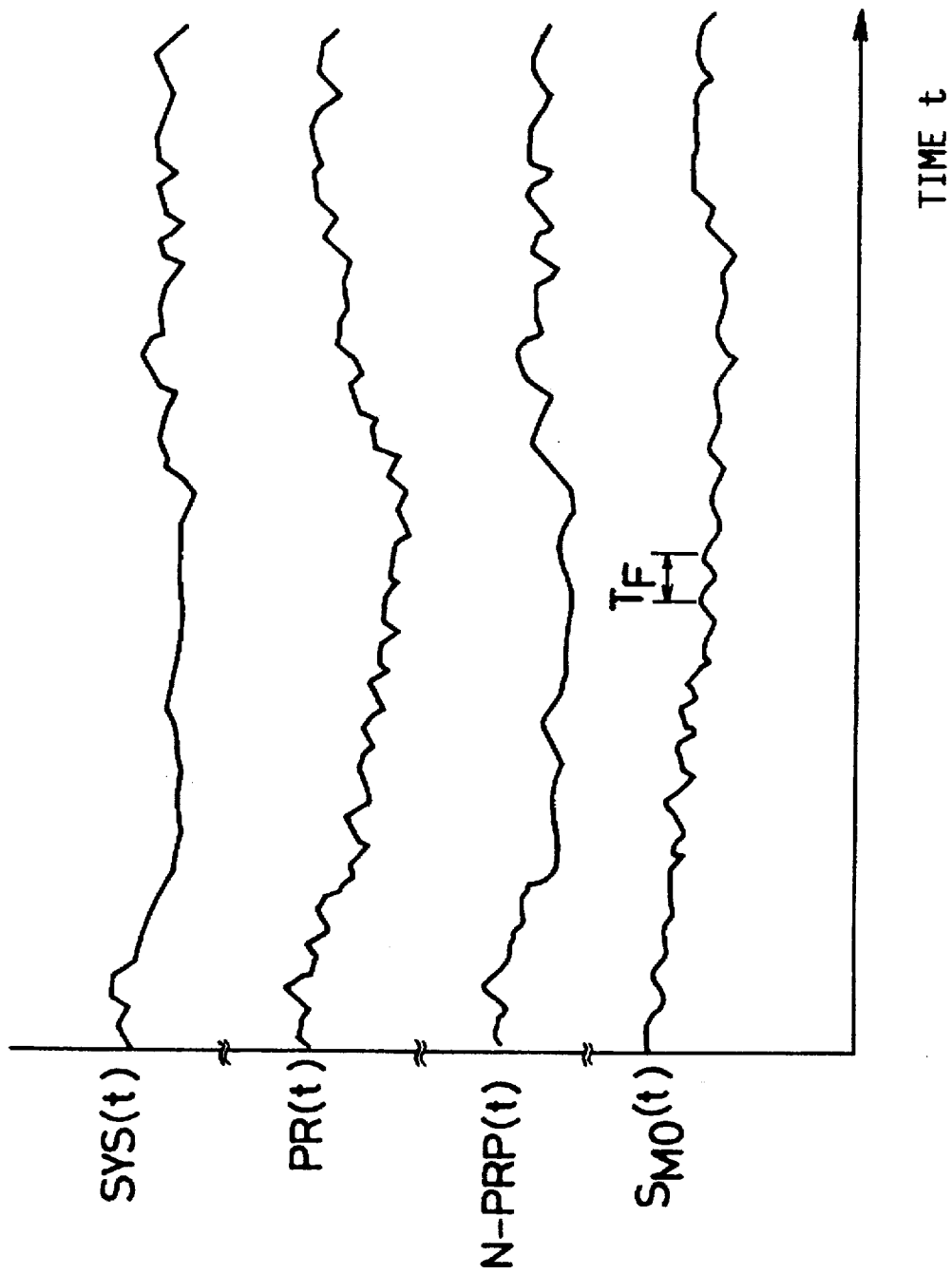
FIG. 9 is a time chart showing a period, $T_F$, of cyclic change of weighted areas, $S_{MO}(t)$, iteratively calculated in the third embodiment.

In the expression (5), the weight changes as the time t proceeds toward the end of the time duration $t_L$ (=$T_M/2$). FIG. 8 shows two pulse wave signals SM, indicated in solid and broken lines, respectively, which have waveforms inverted from each other. Even in the case where the two one-pulse signals SM may have an equal area $S_M$, they would probably have different weighted areas $S_{MO}$. Thus, the weighted areas $S_{MO}$ can identify the difference between the respective waveforms of the two one-pulse signals SM which may not be identified by the non-weighted areas $S_M$. The respiration rate measuring apparatus in accordance with the third embodiment enjoys the same advantages as those of the second embodiment. Additionally, the weighted areas SM have more distinctive upper peaks than those of the products N–PRP obtained in the first embodiment, as shown in the graph of FIG. 9. Thus, the present apparatus more accurately measures a respiration period $T_F$ and a respiration rate RR of a living subject. Moreover, the weighted area $S_{MO}$ obtained in the third embodiment can more reliably reflect an inverted waveform of each one-pulse signal SM.

Next, there will be described a fourth embodiment of the present invention. In the fourth embodiment, Steps SF3 and SF4 of the flow chart of FIG. 6 for the second and third embodiments are replaced by Steps SG1 through SG7 of the flow chart of FIG. 10. In the second and third embodiments, at Step SF3 the areas $S_M$ or weighted areas $S_{MO}$ are determined as the evaluated values of the respective waveforms of one-pulse signals SM, so that a respiration rate RR of the patient is determined from the period of cyclic change of those values $S_M$ or $S_{MO}$. In the fourth embodiment, the area $S_M$ or the weighted area $S_{MO}$ is replaced by an area, F, of a triangle defined by three points, i.e., Point A corresponding to the upper peak of each one-pulse signal SM, Point B of the same one-pulse signal SM located at one fourth of a period $T_M$ thereof, i.e., half a time duration $t_L/2$, following Point A, and Point C of the same one-pulse signal SM located at half the period $T_M$, i.e., the time duration $t_L$, following Point A, as shown in FIG. 11.

If the measure circuit 14 or CPU 20 receives, from the pulse wave sensor 10, a length of pulse wave signal SM corresponding to a cycle of heartbeat (i.e., one pulse) of the patient, and normalizes the one-pulse signal SM, then the control of the CPU 20 goes to Step SG1 to determine three points A, B, and C with respect to the waveform of the one-pulse signal SM. As described above, those three points are Point A corresponding to the upper peak of the one-pulse signal SM, Point B of the same one-pulse signal SM at one fourth of a period $T_M$ thereof following Point A, and Point C of the same one-pulse signal SM at half the period $T_M$ following Point A.

Step SG1 is followed by Step SG2 to compare the respective magnitudes of points B and C with each other. The magnitude of each point A, B, C corresponds to a blood pressure value of the patient. In a first case where the one-pulse signal SM has the waveform as shown in FIG. 11, i.e., if the magnitude of point B is greater than that of point C (i.e., B>C), the control of the CPU 20 goes to Step SG3 to select a sixth expression (6) from three expressions additionally including a seventh and an eighth expression (7) and (8):

$$F=(a'/2)[2c''-(a''+3b'')] \quad (6)$$

$$F=(a'/2) \times c'' \quad (7)$$

$$F=(a'/2)(3b''+2c''-a'') \quad (8)$$

Figure 12:
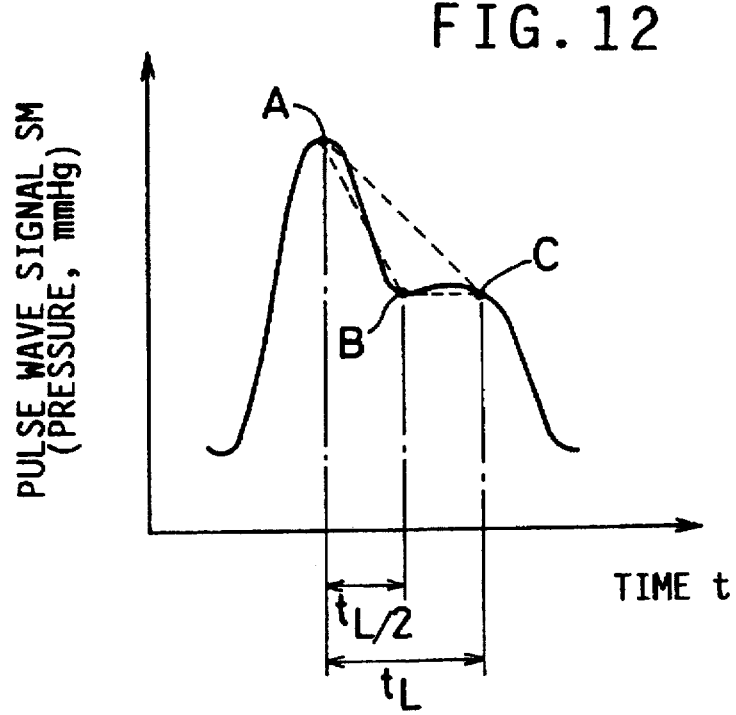
FIG. 12 is a graph showing a pulse wave signal SM having a triangle ABC whose area F is calculated according to an expression (7) in the fourth embodiment.
Figure 13:
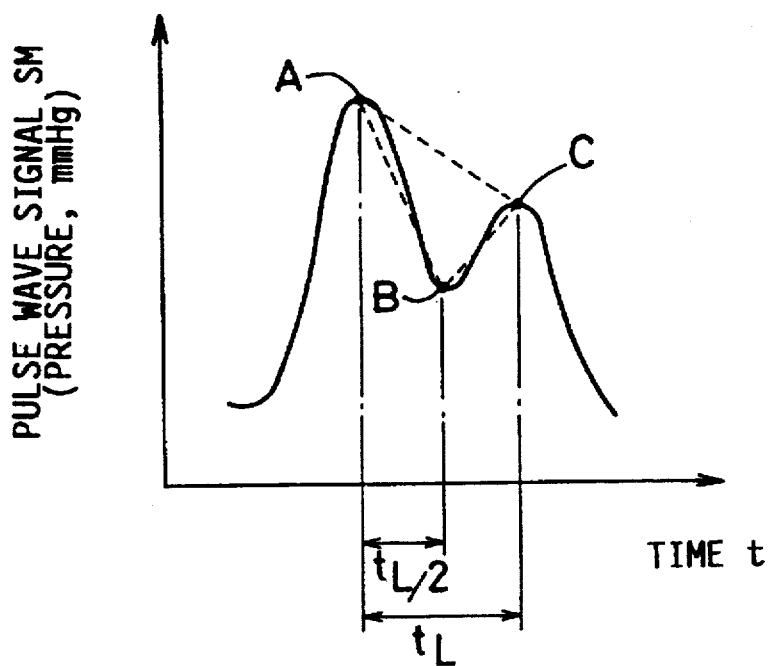
FIG. 13 is a graph showing a pulse wave signal SM having a triangle ABC whose area F is calculated according to an expression (8) in the fourth embodiment.

Meanwhile, in a second case where the one-pulse signal SM has a waveform as shown in FIG. 12, i.e., if the magnitude of point B is equal to that of point C (i.e., B=C), the control of the CPU 20 goes to Step SG4 to select the seventh expression (7). On the other hand, in a third case where the one-pulse signal SM has a waveform as shown in FIG. 13, i.e., if the magnitude of point B is smaller than that of point C (i.e., B<C), the control of the CPU 20 goes to Step SG5 to select the eighth expression (8). Alternatively, the CPU 20 may be programmed such that the CPU 20 selects, at each of Steps SG3, SG4, and SG5, a corresponding map from three maps pre-stored in the ROM 22. Each map defines a relationship between or among two or more parameters a', a'', b'', and c'', for providing an area F of a triangle ABC.

Figure 14:
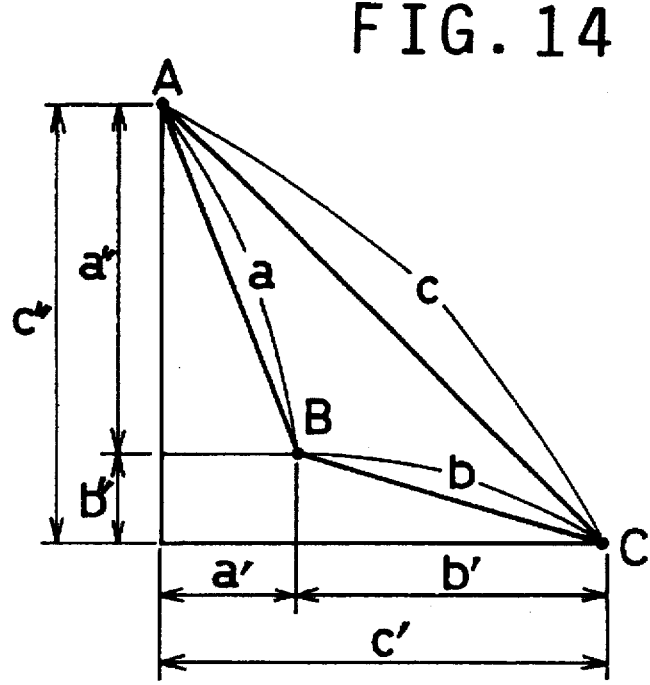
FIG. 14 is a view showing a manner in which the expression (6) is obtained from a triangle ABC.
Figure 15:
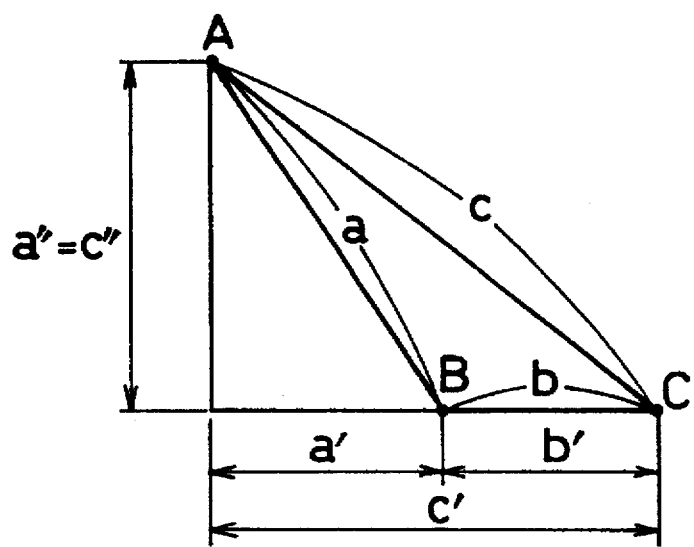
FIG. 15 is a view showing a manner in which the expression (7) is obtained from a triangle ABC.
Figure 16:
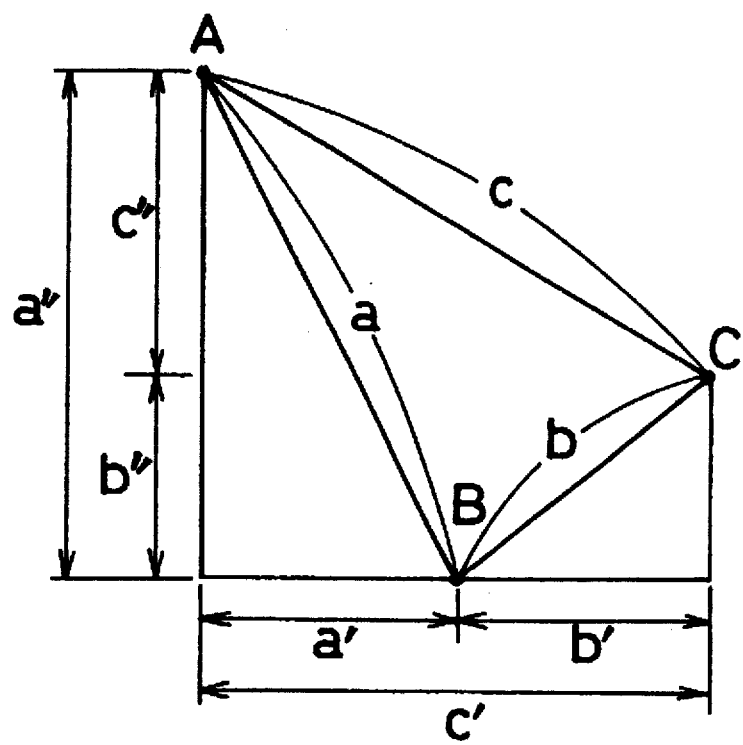
FIG. 16 is a view showing a manner in which the expression (7) is obtained from a triangle ABC.

The sixth expression (6) is obtained using parameters, a', b', c', a'', b'', and c'', shown in FIG. 14, which are applicable to the triangle ABC of FIG. 11, by considering the condition that the length a' is equal to the length b' (i.e., a'=b'). Similarly, the seventh expression (7) is obtained using parameters, a', b', c', a'', and c'', shown in FIG. 15, which are applicable to the triangle ABC of FIG. 12, by considering the conditions that the length a' is equal to the length b' (i.e., a'=b') and the length a'' is equal to the length c'' (i.e., a''=c''). The eighth expression (8) is obtained using parameters, a', b', c', a'', b'', and c'', shown in FIG. 16, which are applicable to the triangle ABC of FIG. 13, by considering the condition that the length a' is equal to the length b' (i.e., a'=b'). The factor, a'/2, of the right-hand side of each of the three expressions (6), (7), and (8) may be omitted, because the periodic change of respective areas F of successive one-pulse signals SM may be identified by comparing the respective evaluated values of one-pulse signals SM obtained according to each expression not containing the factor a'/2. In the present embodiment, the normalization of each one-pulse signal SM carried out at Step SF2 may be omitted. In the latter case, the parameter c'' may be added as a factor to the right-hand side of each of the expressions (6), (7), and (8).

Each of Steps SG3, SG4, and SG5 is followed by Step SG6 to calculate an area F of each of successive one-pulse signals SM, according to the sixth, seventh, or eighth expression selected at Steps SG3, SG4, and SG5. At the following Step SG7, the CPU 20 determines a period of cyclic change, $T_F$, of the respective areas F of the successive one-pulse signals SM, by calculating a time difference between successive two upper peaks of the areas F. Step SG7 is followed by Step SF5 to determine a respiration rate RR of the patient from the thus determined period $T_F$ according to the fourth expression (4).

In the fourth embodiment, Steps SG1 to SG6 correspond to waveform evaluating means. The fourth embodiment enjoys the same advantages as those of the second embodiment. The fourth embodiment enjoys an additional advantage that the CPU 20 automatically selects one of a plurality of expressions (6), (7), and (8) which is suitable for the waveform of a particular one-pulse signal SM. The three waveforms of a one-pulse signal SM, shown in FIGS. 11, 12, and 13, may change with one another, depending upon individual patients and/or locations of wearing of the pulse wave sensor 10. Therefore, in a single continuous respiration rate measurement on a patient, the areas F of successive one-pulse signals SM will be determined according to a single expression initially selected from the expressions (6), (7), and (8).

While the present invention has been described in its preferred embodiments, the invention may otherwise be embodied.

For example, although in the first embodiment shown in FIG. 1 the common or single pulse wave sensor 10 is used for measuring both the pulse rates PR and the systolic blood pressures SYS, an exclusive sensor may be used independent of the pulse wave sensor 10, for exclusively measuring pulse rates PR of a living subject. The exclusive sensor may be (a) a photoelectric sensor which emits a light toward a peripheral portion of a living subject such as a finger, ear lobe, skin, etc. and obtains, in the form of a photoelectric pulse wave signal, the pulsation of a light reflected from, or transmitted through, the peripheral portion; (b) an impedance pulse wave sensor which is worn on a peripheral portion of a living subject and obtains, in the form of an impedance pulse wave signal, the change of impedance of the peripheral portion; or (c) a supersonic pulse wave sensor which detects, using a supersonic wave, a pulse wave as a pulsatile blood current through an artery of a peripheral portion of a living subject, or as a pulsatile motion of the wall of an artery of a peripheral portion of a living subject.

While in the first embodiment two is used as the number n for adjusting the weight of the values SYS(t) relative to that of the values PR(t), the number n may be changed to a different one, such as three, four, or five with or without a fraction for fine adjustment.

While in the second to fourth embodiments the respiration rate RR is determined based on the time change of respective one-pulse waveforms of a pressure pulse wave detected by the pulse wave sensor 10, it is possible to use, in place of the pressure pulse wave, a different pulse wave such as a photoelectric pulse wave, finger-tip pulse wave, impedance pulse wave, or volumetric pulse wave that is optically or electrically detected from a finger or toe of a living subject.

In the first embodiment, at Step SS2, the CPU 20 may be programmed such that the CPU 20 determines, as a pulse rate PR of a patient, a moving average of two or more pulse rate values including the current pulse rate value determined in the current control cycle and one or more pulse rate values determined before one or more control cycles, respectively. Similarly, at Step SS3, the CPU 20 may be programmed such that the CPU 20 determines, as a systolic blood pressure SYS of a patient, a moving average of two or more systolic blood pressure values including the current systolic blood pressure value determined in the current control cycle and one or more systolic blood pressure values determined before one or more control cycles, respectively.

Figure 10:
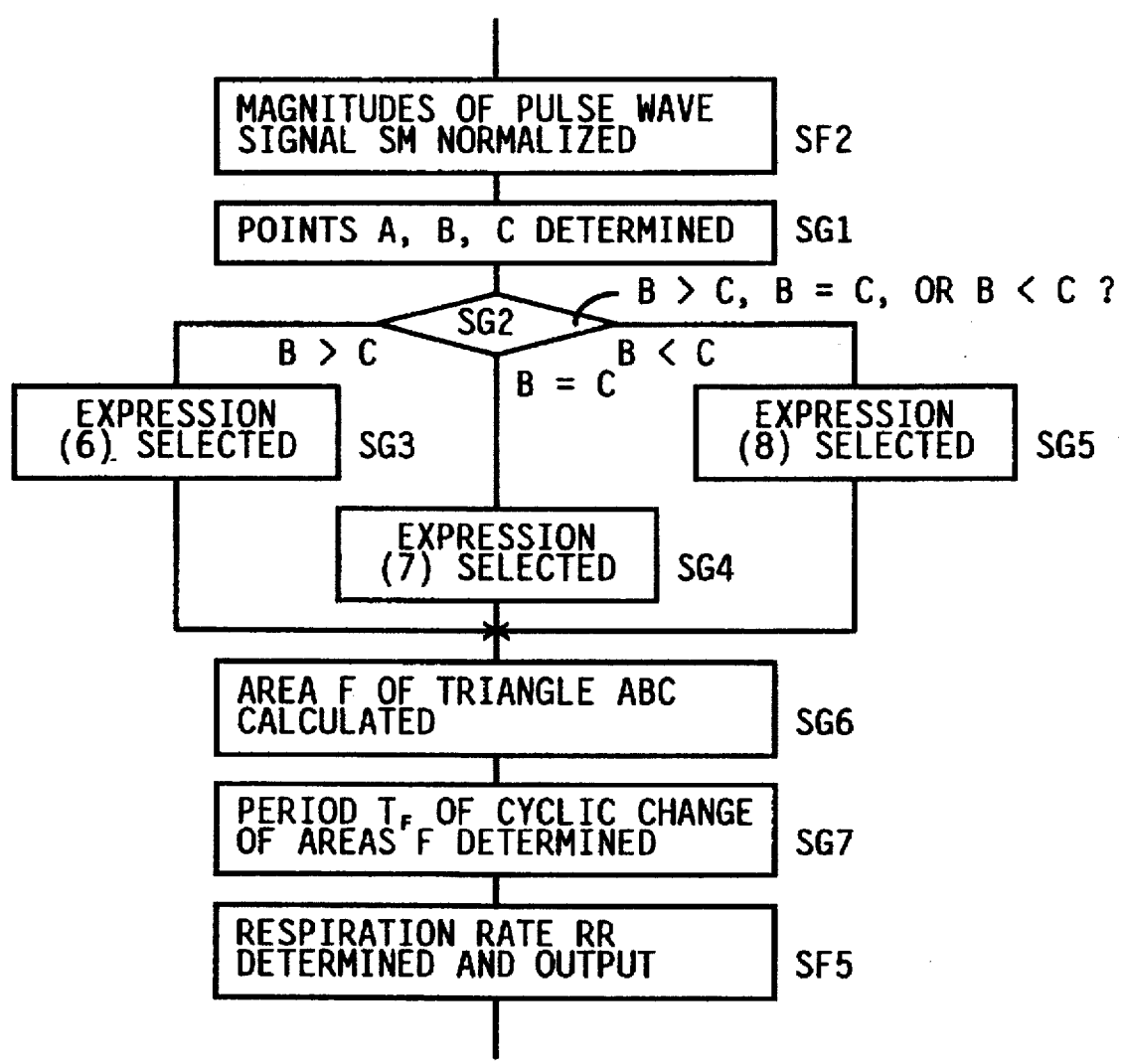
FIG. 10 is a flow chart representing a control program employed in yet another respiration rate measuring apparatus as a fourth embodiment of the invention.
Figure 11:
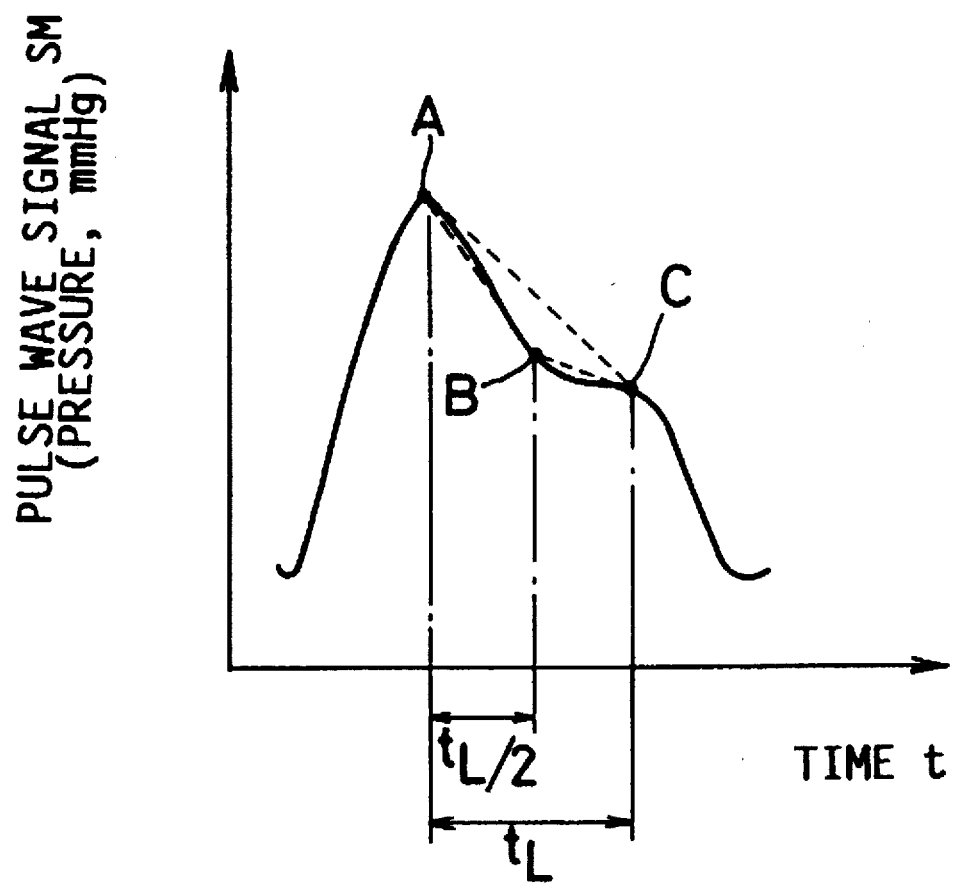
FIG. 11 is a graph showing a pulse wave signal SM having a triangle, ABC, whose area, F, is calculated according to an expression (6) in the fourth embodiment.

In the fourth embodiment, the seventh expression (7) selected at Step SG4 of FIG. 10 may be replaced by a gradient (e.g., 100×a"/c') of a straight line passing through Points A and C of the triangle ABC shown in FIG. 12. This gradient qualifies the waveform of each one-pulse signal SM, like the area F of the triangle ABC.

It is to be understood that the present invention may be embodied with other changes, improvements, and modifications that may occur to those skilled in the art without departing from the scope and spirit of the invention defined in the appended claims.

What is claimed is:

1. An apparatus for measuring a respiration rate of a living subject, comprising:

a pulse rate measuring device which iteratively determines a pulse rate of said subject based on a first pulse wave continuously produced from a peripheral portion of the subject in synchronism with heartbeat of the subject;

a systolic blood pressure measuring device which iteratively determines a systolic blood pressure of said subject based on a magnitude of a second pressure pulse wave continuously produced from an arterial vessel of an extremity of the subject in synchronism with said heartbeat of the subject;

calculating means for iteratively calculating a product of at least two factors which include one of the pulse rates iteratively determined by said pulse rate measuring device and one of the systolic blood pressures iteratively determined by said systolic blood pressure measuring device; and respiration rate determining means for determining said respiration rate of said subject based on a period of a cyclic change of the products iteratively calculated by said calculating means.

2. An apparatus according to claim 1, wherein said calculating means comprises means for iteratively calculating, as said product of said at least two factors, a value, N–PRP(t), according to a following expression:

$$N\text{-}PRP(t)=PR(t)\times[SYS(t-i)/n]$$

where PR(t) is a pulse rate determined by said pulse rate measuring device,

SYS(t) is a systolic blood pressure determined by said systolic blood pressure measuring device, t is time, i is a time lag between PR(t) and SYS(t−i), and n is a number greater than one.

3. An apparatus according to claim 2, wherein said time lag i is a constant value.

4. An apparatus according to claim 2, wherein said calculating means further comprises means for iteratively determining said time lag i by calculating a time difference between (a) a time of occurrence of each of successive upper peaks of a first curve representing the pulse rates PR(t) iteratively determined by said pulse rate measuring device and (b) a time of occurrence of a corresponding one of successive upper peaks of a second curve representing the systolic blood pressure values SYS(t) iteratively determined by said systolic blood pressure measuring device.

5. An apparatus according to claim 1, wherein said pulse rate measuring device comprises:

a pulse wave sensor which detects said first pulse wave continuously produced from said peripheral portion of said subject in synchronism with said heartbeat of the subject;

means for iteratively determining a period, $T_M$, of a cyclic change of said first pulse wave detected by said pulse wave sensor, by calculating a time difference between respective times of occurrence of two successive upper peaks of said first pulse wave; and means for iteratively determining, as a pulse rate, PR, of said subject, a number of upper peaks of said first pulse wave per minute, based on the determined period $T_M$, according to a following expression: $PR=60/T_M$.

6. An apparatus according to claim 1, wherein said systolic blood pressure measuring device comprises:

a pressure pulse wave sensor which detects said second pressure pulse wave continuously produced from said arterial vessel of said extremity of said subject in synchronism with said heartbeat of the subject; and means for iteratively determining, as said systolic blood pressure of said subject, a pressure of each of upper peaks of said pressure pulse wave detected by said pressure pulse wave sensor.

7. An apparatus according to claim 6, wherein said pulse rate measuring device comprises said pressure pulse wave sensor which detects said second pressure pulse wave providing said first pulse wave.

8. An apparatus according to claim 6, wherein said pulse rate measuring device comprises a pulse wave sensor which detects said first pulse wave different from said second pressure pulse wave.

9. An apparatus according to claim 8, wherein said pulse wave sensor comprises one selected from the group consisting of a photoelectric pulse wave sensor, an impedance pulse wave sensor, and a supersonic pulse wave sensor.

10. An apparatus according to claim 1, wherein said respiration rate determining means comprises:

means for determining a period, $T_R$, of a cyclic change of said products iteratively calculated by said calculating means, by calculating a time difference between respective times of occurrence of two successive upper peaks of said products; and means for determining, as a respiration rate, RR, of said subject, a number of upper peaks of said products per minute, based on the determined period $T_R$, according to a following expression: $RR=60/T_R$.

11. An apparatus according to claim 1, further comprising an output device comprising at least one of (a) a display which displays said respiration rate of said subject determined by said respiration rate determining means and (b) a recorder which records, on a recording medium, said respiration rate of said subject determined by said respiration rate determining means.

* * * * *